United States Patent [19]

Ishiguri et al.

[11] Patent Number: 4,584,309

[45] Date of Patent: Apr. 22, 1986

[54] FUNGICIDAL COMPOSITIONS CONTAINING MIXTURES OF A SUBSTITUTED TRIAZOLE-1-PENTEN-3-OL COMPOUND WITH OTHER FUNGICIDES SUCH AS TETRACHLOROISOPHTHALONITRILE

[75] Inventors: Yukio Ishiguri; Hirotaka Takano, both of Takarazuka; Yuji Funaki, Funabashi, all of Japan

[73] Assignee: Sumitomo Chemical Company, Limited, Osaka, Japan

[21] Appl. No.: 737,909

[22] Filed: May 28, 1985

Related U.S. Application Data

[63] Continuation of Ser. No. 498,017, May 25, 1983, abandoned.

[30] Foreign Application Priority Data

| | | | |
|---|---|---|---|
| May 27, 1982 | [JP] | Japan | 57-91000 |
| May 27, 1982 | [JP] | Japan | 57-91001 |
| May 28, 1982 | [JP] | Japan | 57-91930 |
| May 31, 1982 | [JP] | Japan | 57-93787 |

[51] Int. Cl.$^4$ ............................................. A01N 43/64
[52] U.S. Cl. .................................................... 514/383
[58] Field of Search ........................................ 514/383

[56] References Cited

U.S. PATENT DOCUMENTS

Re. 31,693 10/1984 Brandes et al. ..................... 424/164
4,251,512 2/1981 Brandes et al. ..................... 424/164

FOREIGN PATENT DOCUMENTS 2332707 6/1977 France .
2046260 12/1980 United Kingdom .

OTHER PUBLICATIONS

Agricultural Chemicals, Book IV-Fungicides, pp. 114, 168, 307, 324, 325, 437, 544 and 549 (1975).

Primary Examiner—Allen J. Robinson
Attorney, Agent, or Firm—Stevens, Davis, Miller & Mosher

[57] ABSTRACT

A fungicidal composition containing as an active ingredient a mixture of (E)-1-(2,4-dichlorophenyl)-4,4-dimethyl-2-(1,2,4-triazol-1-yl)-1-penten-3-ol and a member selected from an N, N'-ethylenebis(dithiocarbamate) fungicide, tetrachloroisophthalonitrile, N-dichlorofluoromethylthio-N',N'-dimethyl-N-phenylsulfamide and an N-(3,5-dichlorophenyl)imide fungicide in the ratio of 1 to 0.5 - 20 by weight in a total amount of 0.1 to 99.9% by weight, and an inert carrier.

3 Claims, No Drawings

FUNGICIDAL COMPOSITIONS CONTAINING MIXTURES OF A SUBSTITUTED TRIAZOLE-1-PENTEN-3-OL COMPOUND WITH OTHER FUNGICIDES SUCH AS TETRACHLOROISOPHTHALONITRILE This application is a Continuation of application Ser. No. 498,017, filed May 25, 1983, now abandoned.

The present invention relates to a fungicidal composition comprising, as active ingredients, a mixture of (E)-1-(2,4-dichlorophenyl)-4,4-dimethyl-2-(1,2,4-triazol-1-yl)-1-penten-3-ol (hereinafter referred to as "Compound A") and a member selected from an N,N'-ethylenebis(dithiocarbamate) fungicide, tetrachloroisophthalonitrile (hereinafter referred to as "Chlorothalonil"), N-dichlorofluoromethylthio-N',N'-dimethyl-N-phenylsulfamide (hereinafter referred to as "Dichlofluanid") and an N-(3,5-dichlorophenyl)imide fungicide. The N,N'-ethylenebis(dithiocarbamate) fungicide may be manganese ethylenebis(dithiocarbamate) (hereinafter referred to as "Maneb"), zinc ethylenebis(dithiocarbamate) (hereinafter referred to as "Zineb") or zinc manganese ethylenebis(dithiocarbamate) (hereinafter referred to as "Mancozeb"), and the N-(3,5-dichlorophenyl)imide fungicide may be N-(3,5-dichlorophenyl)-1,2-dimethylcyclopropane-1,2-dicarboximide (hereinafter referred to as "Procymidone"), 3-(3,5-dichlorophenyl)-N-isopropyl-2,4-dioxoimidazolidine-1-carboxamide (hereinafter referred to as "Iprodione") or 3-(3,5-dichlorophenyl)-5-methyl-5-vinyloxazolidine-2,4-dione (hereinafter referred to as "Vinclozolin").

As described in Agricultural Chemicals, Book IV-Fungicides (1975) (Thomson Publications), N,N'-ethylenebis(dithiocarbamate) fungicides, Chlorothalonil and Dichlofluanid are known as preventive agents for controlling plant diseases caused by Phycomycetes, but these fungicides are not always satisfactory in preventive and curative effects in controlling diseases such as powdery mildews and rusts. As described in The Pesticide Manual, 6th Edition, N-(3,5-dichlorophenyl)imide fungicides are known as preventive and curative agents for controlling sclerotinia rots and gray molds of various crops and gray spots of fruit trees, but these fungicides are not satisfactory in preventive effects in controlling important diseases such as powdery mildews.

As disclosed in U.K. Patent Application GB No. 2046260A, Compound A has sufficient controlling effect on powdery mildews and rusts of cereal plants, fruit trees and vegetables, but not always on diseases, such as late blights and downy mildews caused by Phytomycetes and gray molds and sclerotinia rots.

The object of this invention is to provide a preventive and/or curative fungicidal composition that can simultaneously control various plant diseases at the lowest possible doses and maintain its preventive and/or curative effect.

The above object and others are accomplished by providing a fungicidal composition comprising as an active ingredient, a mixture of Compound A and a fungicide selected from the N,N'-ethylenebis(dithiocarbamate) fungicides, Chlorothalonil, Dichlofluanid and the N-(3,5-dichlorophenyl)imide fungicides in a ratio of 1:0.5–1:20, preferably 1:1–1:10, by weight.

The fungicidal composition of the present invention has preventive and/or curative effect on the following plants (diseases: Rice (*Pyricularia oryzae; Cochliobolus miyabeanus; Rhizoctonia solani*), wheat, barley, and the like (*Erysiphe graminis f. sp. hordei, f. sp. tritici; Gibberella zeae; Puccinia striiformis, P. graminis, P. recondite, P. hordei; Typhula sp., Micronectriella nivalis; Ustilago tritici, U. nuda; Pseudocercosporella herpotrichoides; Rhynchosporium secalis; Septoria tritici; Leptosphaeria nodorum*), citrus fruits (*Diaporthe citri; Elsinoe fawcetti; Penicillium digitatum, P. italicum*), apple (*Sclerotinia mali; Valsa mali; Podosphaera leucotricha; Alternaria mali; Venturia inaequalis*), pear (*Venturia nashicola; Alternaria kikuchiana; Gymnosporangium haraeanum*), peach (*Sclerotinia cinerea; Cladosporium carpophilum; Phomopsis sp.*), grape (*Elsinoe ampelina; Glomerella cingulate; Uncinula necator; Phakopsora ampelopsidis*), persimmon (*Gloeosporium kaki; Cercospora kaki; Mycosphaerella nawae*), melons (*Colletotrichum lagenarium; Sphaerotheca fuliginea; Mycosphaerella melonis*), tomato (*Alternaria solani; Cladosporium fulvum*), eggplant (*Phomopsis vexans; Erysiphe cichoracearum*), vegetables of rape family (*Alternaria japonica; Cercosporella brassicae*), stone-leek (*Puccinia allii*), soybean (*Gercospora kikuchii; Elsinoe glycines; Diaporthe phaseolorum var. sojae*), kidny bean (*Colletotrichum lindemuthianum*), peanut (*Mycosphaerella personatum; Cercospora arachidicola*), pea (*Erysiphe pisi*), potato (Alternaria solani), strawberry (*Sphaerotheca humuli*), tea (*Exobasidium reticulatum; Elsinoe leucospila*), tobacco (*Alternaria longipes; Erysiphe cichoracearum; Collectotrichum tabacum*), sugar beat (*Cercospora beticola*), rose (*Diplocarpon rosae; Sphaerotheca pannosa*), chrysanthemum (*Septoria, chrysanthemiindici; Puccinia horiana*), various crops (*Botrytis cinerea; Sclerotinia sclerotiorum*), and so forth.

And, examples of phytopathogenic fungi belonging to Phycomycetes are as follows:

Peronospora brassicae on vegetables and radish, Peronospora spinaciae on spinach, Peronospora tabacina on tobacco, Pseudoperonospora cubensis on cucumber, Plasmorpara viticola on grape, Plasmopara nivea on Umbelliferae plants, Phytophthora cactorum on apple, strawberry and carrot, Phytophthora capsici on tomato and cucumber, Phyotphthora cinnamomi on pineapple, Phytophthora infestans, on potato, tomato and eggplant, Phytophthora nicotianae var. nicotianae on tobacco, kidney bean and onion, Pythium aphanidermatum on cucumber, Pythium sp. on spinach, Pythium sp. on wheat, Pythium debaryanum on tobacco, Pythium rot (i.e. P. aphanidermatum, P. debaryanum, P. irregulare, P. myriotylum, P. ultimum*) on soybean and so forth.

The fungicidal composition of this invention is applied to paddy fields, wheat fields, other cereal or vegetable fields, orchards, tea gardens, meadows, lawns, etc.

Although the mixture contained as the active ingredient in the present fungicidal composition may be applied as such, it is usually used in the form of wettable powder, flowable, granule, dust, or others, which can be prepared by mixing a solid carrier, liquid carrier, surfactant, or other adjuvant. These forms of compositions contain 0.1–99.9%, preferably 1–99% by weight of the active ingredient mixture.

Solid carriers usable for the composition include fine powders or granules of kaolin, attapulgite clay, bentonite, acid clay, pyrophyllite, talc, diatomaceous earth, calcite, corn kernel meal, walnut shell meal, urea, ammonium sulfate, and synthetic hydrated silica. Usable liquid carriers include aromatic hydrocarbons such as xylene and methylnaphthalene; alcohols such as isopropanol, ethylene glycol, and Cellosolve; ketones such as acetone, cyclohexanone, and isophorone; vegetable oils such as soybean oil and cotton seed oil; dimethylsulfoxide, acetonitrile, and water.

Surfactants to be used for emulsifying, dispersing, or wetting-spreading the fungicide include anionic surfactants such as alkyl sulfate salts, alkylsulfonate or arylsulfonate salts, dialkyl sulfosuccinate salts, polyoxyethylene alkyl aryl ether phosphate satls, and naphthalenesulfonic acid-formalin condensation product; and nonionic surfactants such as polyoxyethylene alkyl ethers, polyoxyethylenepolyoxypropylene block copolymer, sorbitan-fatty acid esters, and polyoxyethylene sorbitan-fatty acid esters. The adjuvants include ligninsulfonic acid salts, alginic acid salts poly(vinyl alcohol), gum arabic, CMC (carboxymethyl-cellulose), and PAP (isopropyl acid-phosphate).

Formulation of the fungicidal composition of this invention is illustrated by the following Formulation Examples, wherein parts are by weight.

FORMULATION EXAMPLE 1

A wettable powder was formulated by good mixing and grinding of 5 parts of Compound A, 50 parts of Maneb, 3 parts of calcium ligninsulfonate, 2 parts of sodium lauryl sulfate, and 40 parts of synthetic hydrated silica.

FORMULATION EXAMPLE 2

A granular composition was formulated by good mixing and grinding of 0.5 part of Compound A, 2.5 parts of Chlorothalonil, 1 part of synthetic hydrated silica, 2 parts of calcium ligninsulfonate, 30 parts of bentonite, and 64 parts of kaolin, and thoroughly kneading the mixture in the presence of water, followed by granulating and drying.

FORMULATION EXAMPLE 3

A flowable composition was formulated by mixing 5 parts of Compound A, 20 parts of Dichlofluanid, 3 parts of polyoxyethylenesorbitan monooleate, 3 parts of CMC, and 69 parts of water, and grinding the mixture in wet form to particle sizes of the active ingredients of $5\mu$ and less.

FORMULATION EXAMPLE 4

A dust composition was formulated by thoroughly mixing and grinding 0.5 part of Compound A, 1.5 parts of Procymidone, 88 parts of kaolin, and 10 parts of talc.

These fungicidal compositions are applied as such or after dilution with water, to leaves and steams (or stalks) by spraying or to soil as dusts or granules by mixing therewith. Enhanced fungicidal efficacy is expected when these compositions are served in mixture with some other fungicides. They also can be applied in combination with an insecticide, acaricide, nematocide, herbicide, plant growth regulator, fertilizer, or soil quality improver.

The compositions of the invention are generally applied in doses of 1–1,000 g, preferably of 10–500 g per acre in terms of the active ingredient mixture. When they are applied in the form of wettable powder or flowable the total concentration of the active ingredient mixture ranges from 0.001 to 1%, preferably from 0.01 to 0.5%, by weight. In the form of granule or dust, they are applied without dilution.

The plant-disease controlling effect of the composition of this invention is illustrated with reference to the following Test Examples. In some of the Examples, besides the present active ingredients, the following compounds were employed as comparative active ingredients:

| Compound | Structure | Remarks |
| --- | --- | --- |
| B | $\left[ \begin{array}{c} C_2H_5O \quad O \\ \diagdown \quad \diagup \\ P \\ \diagup \quad \diagdown \\ H \quad O^- \end{array} \right]_3 Al^{3+}$ | Commercially available fungicide "aliette" |
| C | (structure: triazine ring with Cl substituents and NH-phenyl-Cl group) | Triazine fungicide |

The effect was evaluated by visual observation of test plants to examine symptoms, viz. the growth extents of fungus colonies and of sick spots on the leaves and stems. Criteria of the evaluation are as follows:

Rating 5: None of said colonies and spots were observed.
Rating 4: Said colonies and spots were observed on about 10% of the leaves and stems.
Rating 3: They were observed on about 30% of the leaves and stems.
Rating 2: They were observed on about 50% of the leaves and stems.
Rating 1: They were observed on about 70% of the leaves and stems.
Rating 0: Symptoms were as remarkable as in the case of the control (no fungicide was applied).

TEST EXAMPLE 1

(Preventive effect on cucumber gray mold)

Cucumbers (var. Sagamihanjiro) were seeded in plastic pots filled with sand soil, and were grown for 8 days in a green house. Resulting cucumber seedlings, which had developed cotyledons, were sprayed with individual fungicidal flowable that had been formulated in accordance with Formulation Example 3 and diluted with water to predetermined concentrations. Then, agar pieces containing a cucumber gray mold fungus were stuck onto the seedlings to inoculate the fungus thereupon. The seedling were further grown for 3 days at 20° C. under a high humidity condition, to examine the controlling effect. The results are shown in Table 1.

TABLE 1

| Active ingredient | Concentration of active ingredient applied (ppm) | Controlling effect (rating) |
| --- | --- | --- |
| A | 150 | 4 |
| A | 125 | 3 |
| A | 100 | 2 |
| A | 25 | 1 |
| Chlorothalonil | 125 | 2 |
| " | 100 | 2 |
| Dichofluanid | 100 | 2 |
| " | 75 | 2 |
| Procymidone | 150 | 4 |
| " | 100 | 2 |
| Iprodione | 150 | 3 |
| " | 100 | 2 |
| Vinclozolin | 150 | 4 |
| " | 100 | 2 |

TABLE 1-continued

| Active ingredient | Concentration of active ingredient applied (ppm) | Controlling effect (rating) |
|---|---|---|
| A + Chlorothalonil | 25 + 100 | 5 |
| A + Dichlofluanid | 25 + 75 | 5 |
| A + Procymidone | 50 + 100 | 5 |
| A + Iprodione | 50 + 100 | 5 |
| A + Vinclozolin | 50 + 100 | 5 |
| C | 150 | 4 |

TEST EXAMPLE 2

(Preventive effect on cucumber downy mildew)

Cucumbers (var. Sagamihanjiro) were seeded in plastic pots filled with sand soil, and were grown for 14 days in a green house. Resulting seedlings, which had developed cotyledons, were sprayed with individual fungicidal flowable that had been formulated in accordance with Formulation Example 3 and diluted with water to predetermined concentrations. Then, a cucumber downy mildew fungus was inoculated upon the seedlings by spraying them with a suspension of its spores. The seedlings were further grown for 3 days at 20° C. under a high humidity condition and then for 3 days under illumination, to examine the controlling effect. The results are shown in Table 2.

TABLE 2

| Active ingredient | Concentration of active ingredient applied (ppm) | Controlling effect (rating) |
|---|---|---|
| A | 50 | 2 |
| A | 12.5 | 0 |
| A | 10 | 0 |
| A | 2.5 | 0 |
| Chlorothalonil | 12.5 | 4 |
| " | 10 | 3 |
| Dichlofluanid | 50 | 3 |
| " | 40 | 2 |
| A + Chlorothalonil | 2.5 + 10 | 5 |
| A + Dichlofluanid | 10 + 40 | 5 |
| B | 50 | 3 |

TEST EXAMPLE 3

(Preventive effect on cucumber anthracnose)

Cucumbers (var. Sagamihanjiro) were seeded in plastic pots filled with sand soil and were grown for 8 days in a green house. Resulting seedlings, which had developed cotyledons were sprayed with individual fungicidal flowable that had been formulated in accordance with Formulation Example 3 and diluted with water to predetermined concentrations. Then, a cucumber anthracnose fungus was inoculated upon the seedlings by spraying them with a suspension of its spores. The seedlings were further grown for 2 days at 23° C. under a high humidity condition and then for 3 days under illumination, to examine the controlling effect. The results are shown in Table 3.

TABLE 3

| Active ingredient | Concentration of active ingredient applied (ppm) | Controlling effect (rating) |
|---|---|---|
| A | 125 | 3 |
| A | 100 | 3 |
| A | 25 | 0 |

TABLE 3-continued

| Active ingredient | Concentration of active ingredient applied (ppm) | Controlling effect (rating) |
|---|---|---|
| Maneb | 100 | 2 |
| Maneb | 75 | 2 |
| Zineb | 100 | 3 |
| Zineb | 75 | 2 |
| Mancozeb | 100 | 4 |
| Mancozeb | 75 | 3 |
| Chlorothalonil | 125 | 4 |
| Chlorothalonil | 100 | 3 |
| A + Maneb | 25 + 75 | 5 |
| A + Zineb | 25 + 75 | 5 |
| A + Mancozeb | 25 + 75 | 5 |
| A + Chlorothalonil | 25 + 100 | 5 |
| C | 125 | 4 |

TEST EXAMPLE 4

(Curative effect on tomato late blight)

Tomato (var. Ponteroza) was seeded in plastic pots filled with sand soil and grown for 20 days in a green house. A tomato late blight fungus was inoculated upon resulting tomato seedlings, which had just developed the second regular leaf, by spraying them with a suspension of its spores. After further growth of the seedling for 1 day at 15° C. at a high humidity condition, individual fungicidal flowable that had been formulated in accordance with Formulation Example 3 and diluted with water to predetermined concentrations were sprayed to adhere sufficiently to the leaves of the seedlings. Thereafter, the seedlings were grown for 6 days at 15° C. under illumination to examine the controlling effect. The results are shown in Table 4.

TABLE 4

| Active ingredient | Concentration of active ingredient applied (ppm) | Controlling effect (rating) |
|---|---|---|
| A | 500 | 4 |
| A | 100 | 3 |
| Maneb | 500 | 0 |
| Maneb | 400 | 0 |
| Zineb | 500 | 0 |
| Zineb | 400 | 0 |
| Mancozeb | 500 | 0 |
| Mancozeb | 400 | 0 |
| Chlorothalonil | 500 | 0 |
| Chlorothalonil | 400 | 0 |
| Dichlofluanid | 500 | 0 |
| Dichlofluanid | 400 | 0 |
| A + Maneb | 100 + 400 | 5 |
| A + Zineb | 100 + 400 | 5 |
| A + Mancozeb | 100 + 400 | 5 |
| A + Chlorothalonil | 100 + 400 | 5 |
| A + Dichlofluanid | 100 + 400 | 5 |
| B | 500 | 3 |

TEST EXAMPLE 5

(Preventive effect on kidney bean stem rot)

Kidney bean (var. Nagauzuramame) was seeded in plastic pots filled with sand soil and grown for 20 days in a green house. Resulting seedlings, which had developed the second regular leaf, were sprayed with individual fungicidal flowable that had been formulated in accordance with Formulation Example 3 and diluted with water to predetermined concentrations. After spraying, an agar piece containing organisms causing stem rot of kidney bean was reared at 20° C. for 5 days in high humidity and the control effect was examined. The results are shown in Table 5.

TABLE 5

| Active ingredient | Concentration of active ingredient applied (ppm) | Controlling effect (rating) |
| --- | --- | --- |
| A | 100 | 3 |
| A | 25 | 1 |
| Procymidone | 100 | 4 |
| Procymidone | 75 | 3 |
| Iprodione | 100 | 3 |
| Iprodione | 75 | 2 |
| Vinclozolin | 100 | 3 |
| Vinclozolin | 75 | 2 |
| A + Procymidone | 25 + 75 | 5 |

TABLE 5-continued

| Active ingredient | Concentration of active ingredient applied (ppm) | Controlling effect (rating) |
| --- | --- | --- |
| A + Iprodione | 25 + 75 | 5 |
| A + Vinclozolin | 25 + 75 | 5 |
| C | 100 | 4 |

What is claimed is:

1. A fungicidal composition containing as an active ingredient, 0.1 to 99.9% by weight of a mixture of (E)-1-(2,4-dichlorophenyl)-4,4-dimethyl-2-(1,2,4-triazol-1-yl)-1-pentene-3-ol and tetrachloroisophthalonitrile in the mixing ratio of 1:1 to 1:10 by weight and an inert carrier.

2. The composition according to claim 1 wherein the amount of said mixture is 1 to 99% by weight.

3. A method for controlling a fungus which comprises contacting said fungus with a fungicidally effective amount of the composition according to claim 1.

* * * * *